United States Patent [19]

Schillinger

[11] Patent Number: 5,576,473

[45] Date of Patent: Nov. 19, 1996

[54] INBRED CORN LINE 7054

[75] Inventor: John A. Schillinger, Kalamazoo, Mich.

[73] Assignee: Asgrow Seed Company, Kalamazoo, Mich.

[21] Appl. No.: 436,350

[22] Filed: Jul. 5, 1995

[51] Int. Cl.$^6$ .............................. A01H 5/00; A01H 4/00; A01H 1/00; C12N 5/04

[52] U.S. Cl. .................. 800/200; 800/250; 800/DIG. 56; 435/240.4; 435/240.49; 435/240.5; 47/58; 47/DIG. 1

[58] Field of Search .................................. 800/200, 205, 800/DIG. 56, 250; 47/58; 435/172.3, 172.1, 240.4, 240.45, 240.49, 240.50

[56] References Cited

PUBLICATIONS

Meghji et al. Inbreeding Depression, Inbred & hybrid grain yields and other traits of maize genotypes representing three eras. Crop Science vol. 24, pp. 545–549, 1984.

Hallauer et al., Corn Breeding. In Corn and Corn Improvement, No. 18, ASA, pp. 463–481, 1988.

Wych, Robert D. Production of hybrid seed. In Corn and Corn improvement. Ibid, 1988.

Primary Examiner—Gary Benzion
Attorney, Agent, or Firm—Rothwell, Figg, Ernst & Kurz pc

[57] ABSTRACT

According to the invention there is provided an inbred corn line designated as 7054. This invention thus relates to the plant, ovules, pollen and seed of the inbred and includes the tissue culture which comprising regenerable cells of inbred 7054 and plants produced therefrom. This invention further relates to hybrid plants and seeds produced by crossing inbred 7054, as the male or female plant, to another inbred and methods of hybridization used to produced such hybrids. This invention further relates to corn plants having all the physiological and morphological characteristics inbred corn plant 7054.

11 Claims, No Drawings

INBRED CORN LINE 7054

FIELD OF INVENTION

This invention is in the field of corn breeding, specifically relating to an inbred corn line designated 3087, 5720, 6022 and 7054.

BACKGROUND OF THE INVENTION

The goal of corn breeding is to produce a hybrid which has outstanding agronomic features for a number of traits. The most important trait is typically the grain yield expressed in weight or volume of grain produced per unit area of harvest, e.g., tons/hectare. Several secondary traits, many of which indirectly affect yield, are also important. These traits may include resistance to disease and insects, resistance to lodging, tolerance to heat and drought, length of time to maturity, and quality traits. Any new hybrid developed by breeding techniques must have improvement in enough of these traits to provide a grower an advantage over previously released hybrids.

The breeding and development of new commercial hybrids involves the use of 2 essential techniques: self-pollination and cross-pollination. For self-pollination, the pollen from one plant is placed on the silks of the same plant. For cross-pollination, pollen from one plant is placed on the silks of another plant. When self-pollination is practiced over a series of several generations, the resulting plants become homozygous at almost all gene loci and produce a uniform population of true breeding progeny. Plants at this stage in development are called inbred lines and can be maintained by continued self-pollination.

A cross between two homozygous, inbred lines produces a uniform population of plants referred to as F1 hybrids. F1 is defined as the first filial generation resulting from a cross. While these hybrids are genetically uniform, they are typically heterozygous for many gene loci. A cross of 2 plants that are not inbred will also produce F1 plants with many heterozygous loci; however, the hybrid plants resulting from this cross will not be genetically uniform.

During the self pollination process, inbreeding occurs and the vigor of the lines decrease. The vigor, which is manifested in many ways including increased vegetative growth and increased yield, is restored when two unrelated inbred lines are crossed to produce the F1 hybrid seed. It is important that lines used as parents in commercial FI hybrids be inbred (true breeding) and unrelated. The inbred nature ensures the uniformity of the hybrid, which is essential for mechanical harvesting and it allows the reproduction of the same hybrid year after year. The unrelatedness of the inbred lines maximizes the vigor that result in the F1 hybrids. Hybrids between closely related lines are not as vigorous as from unrelated lines.

A single-cross hybrid is produced when two inbred lines are crossed to produce the F1 progeny. A double-cross hybrid is produced from four inbred lines crossed in pairs (A×B and C×D) and then the two F1 hybrids are crossed again (A×B)×(C×D). Double cross hybrids are not as genetically uniform as single-cross hybrids; however, they can be uniform enough to be acceptable for mechanical harvest procedures used today.

The development of commercial corn hybrids requires: 1) the development of homozygous inbred lines, 2) the crossing of these inbred lines to form hybrids, and 3) the evaluation of these hybrids.

The development of inbred lines most commonly utilizes the pedigree method of breeding. The initial step involves the development of a source population. The source population may consist of an F1 hybrid, or it may consist of a group of plants resulting from cross pollination of several lines. Lines to be included in the source population are selected so that desirable traits from different parental lines will be combined together into the daughter population. This daughter population is self-pollinated several generations, with the best plants selected during each generation of inbreeding. As the lines become more inbred, the genes included in the source population will recombine in new combinations giving a series of new inbred lines, some having desirable traits from different parents involved in the source population.

These new inbred lines are then crossed to other, unrelated inbred lines to produce F1 hybrids which are evaluated in multiple locations for commercial potential. The best F1 hybrids are identified and the inbred lines used to make these F1 hybrids are then increased for commercial production.

Backcrossing can also be used to improve an inbred line. Backcrossing transfers a specific desirable trait from one inbred or source to an inbred that lacks a trait(s). This can be accomplished for example by first crossing a superior inbred (A) (recurrent parent) to a donor inbred (non-recurrent), which carries the appropriate gene(s) for the trait in question. The progeny of this cross is then mated back to the superior recurrent parent (A) followed by selection in the resultant progeny for the desired trait to be transferred from the non-recurrent parent. After several backcross generations, the progeny will contain the new trait in the superior background of the recurrent parent.

Other breeding methods for developing inbred lines include recurrent selection and various modifications of the pedigree method.

While the ultimate goal is to identify superior hybrids, this must be achieved by identifying superior inbred lines as parents of the hybrids.

SUMMARY OF THE INVENTION

According to the invention, there is provided novel inbred corn lines including corn lines 3087, 5720, 6022 and 7054. This invention thus also provides the seeds, plants, and plant parts of inbred corn lines 3087, 5720, 6022 and 7054. This invention further provides methods involving crossing of inbred corn lines 3087, 5720, 6022 and 7054 with each other as well as with other inbred lines to produce commercial F1 hybrids, and to methods of crossing inbred corn lines 3087, 5720, 6022 and 7054 with other plants to produce breeding populations for developing new inbred lines.

DEFINITIONS

In the description of the invention, several terms will be used. The following definitions are given to provide a clear understanding of the specific claims:

Relative maturity is the predicted maturity of hybrids developed from the inbred of the invention and is based on the harvest moisture of the grain at maturity, relative to a set of standard checks.

Yield or YLD is the yield in tons/hectare (tons/ha) of grain at harvest adjusted to 15.5% moisture.

Moisture or MOIS is the actual moisture of the grain at harvest represented as a percent weight of water/weight of grain×100.

Y:MO is a statistic calculated by dividing the yield (in tons/ha) by the moisture (MOIS), multiplied by 100. This statistic expresses yield as a function of moisture. Hybrids which yield high, within its maturity class, will score high with this statistic.

Growing Degree Units or GDU is the number of growing degree units needed for an inbred line or hybrid to reach a certain stage of development. GDU is another method for measuring maturity. Growing degree units are calculated by the Barger Method, where the heat units for a 24 hour period are: GDU=(Max+Min)/2−50, and the highest maximum value used is 86 F. and the lowest minimum used is 50 F.

Stalk lodging or STL is a rating which evaluates the ability of plants to resist stalk breakage. The range in the rating is between 1 and 9. Hybrids scored as 1 have no or few lodged plants (when the stalk breaks or bends below the ear) whereas a rating of 9 indicates that many plants are lodged. The data are given as the mean percentage of the experiments in which the hybrid was grown.

Root lodging or RTL is a rating which evaluates the ability of plants to resist root lodging. The range in the rating is between 1 and 9. Hybrids scored as 1 have no root lodged plants while those scored as 9 have a large percentage of plants which are root lodged. The percentage of root lodged plants is measured at harvest. Plants are considered root lodged when the stalk leans more than 30 degrees from the vertical axis. The data are given as the mean percentage of the experiments in which the hybrid was grown.

Central corn belt or CCB is a measure of the number of days it takes hybrid corn to grow to maturity in the mid-north to northern regions of the US corn belt.

Stay green or SGR is a measure of plant health near the time of black layer formation (physiological maturity). The range in this rating is also between 1 and 9 with low scores indicating better late-season plant health. The data is given as a mean rating for the experiments in which the hybrid was grown.

Field score or FSC is a measure of plant integrity and visual appeal at harvest. The range in this rating is between 1 and 9 with low scores indicating better plant integrity and appearance.

Test weight/hectoliter weight or HLWT is a measure of the density of the grain. It is the weight of the grain in kilograms for a given volume (hectoliter) adjusted for percent moisture. Data is given as a mean weight of the experiments in which the hybrid was grown.

Plant height or PHT is the height of the hybrid or inbred (in centimeters) from the ground to the tip of the tassel. The data is given as the mean height of the experiments in which the inbred or hybrid was grown.

Ear height or EHT is the height of the ear of hybrid or inbred plants (in centimeters) from the ground to the ear node attachment. The data is given as the mean height of the experiment in which the inbred or hybrid was grown.

Restriction Fragment Length Polymorphism or RFLP is a molecular approach for characterizing the genetic makeup of different lines of corn. The data generated from RFLP is presented in molecular weights (MW) of bands identified when DNA from an inbred is cut by a particular enzyme, separated electrophoretically, and hybridized with a particular DNA probe. The molecular weight units are in kilobase pairs, and the DNA probes are publicly available.

DETAILED DESCRIPTION OF THE INVENTION

The inbred corn lines 3087, 5720, 6022 and 7054 of the present invention are a yellow dent corn with superior characteristics and are excellent parental lines in crosses for producing hybrid corn.

Inbred 3087 was selected from a source population made by crossing a number of inbred lines related to Mo17 and Oh43 with the inbred LH123. Standard pedigree ear-row selection for acceptable agronomic types was performed throughout the generations of self pollination. Test crosses with unrelated inbred lines were made and evaluated over multiple locations. One subline within this population had good hybrid performance and appeared acceptable as a male parent. This subline was crossed with several non-related inbred lines from the stiff stalk family and were evaluated throughout the central US cornbelt. This inbred had very good testcross performance with a number of unrelated inbred lines.

The inbred 3087 produces hybrids which are well adapted to central latitudes of the US corn belt, producing hybrids with relative maturity of 100–110 days CCB. Inbred 3087 has good pollen shed and thus serves as a good male parent.

The inbred 3087 has shown uniformity and stability for all traits as described in the following variety description information (Table 1). It has been self-pollinated and ear-rowed a sufficient number of generations with careful attention paid to uniformity of plant type to ensure genetic homozygosity and phenotypic stability. No variant traits are expected in 3087. Table 1 shows the morphological and other characteristics of inbred 3087.

The data in Table 2 shows the relative hybrid performance of 3087 compared to a number of inbred lines which are currently used as males in hybrid production. These inbred lines are either Asgrow proprietary or those from a seed stock company from which Asgrow has a license. The comparisons of 3087 with the other inbred lines was conducted on two testers as indicated in Table 2. In all instances, the 3087 hybrids yielded more than the other parents, with an overall advantage of 0.5 tons/hectare. The 3087 hybrids also were 0.2% drier at harvest, on the average, giving a Y:MO ratio advantage of 3.4. The stay green, stalk lodging, root lodging, and field score, ratings were all comparable. 3087 also produced hybrids that are taller with slightly higher ear placement.

An RFLP profile of inbred 3087 is listed in Table 3. As far as is known, this pattern is unique from those of all other inbreds available.

Inbred seeds of 3087 have been placed on deposit pursuant to the terms of the Budapest Treaty at the American Type Culture Collection (ATCC), Rockville, Md., 20852, under deposit accession number 75337 on 2 November, 1992. A Plant Variety Protection Certificate has also been applied for with the United States Department of Agriculture.

Inbred 5720 was selected from a source population developed by crossing a public inbred line developed at University of Illinois with an inbred line related to Mo17, a popular inbred line developed at University of Missouri. Standard pedigree ear-row selection for acceptable agronomic types was performed throughout the generations of self pollination. Test crosses with unrelated inbred lines were made and evaluated over multiple locations. One subline within this population had good hybrid performance and appeared acceptable as a male parent. This subline was crossed with several non-related inbred lines from the stiff stalk family and were evaluated throughout the central US cornbelt with an emphasis in eastern environments. This inbred had very good testcross performance with a number of unrelated inbred lines.

The inbred 5720 produces hybrids which are well adapted to the eastern half of the US corn belt, producing hybrids with relative maturity of 107–116 days CCB. Inbred 5720 has good pollen shed and thus serves as a good male parent.

The inbred 5720 has shown uniformity and stability for all traits as described in the following variety description information (Table 4). It has been self-pollinated and ear-rowed a sufficient number of generations with careful attention paid to uniformity of plant type to ensure genetic homozygosity and phenotypic stability. No variant traits are expected in 5720. Table 4 shows the morphological and other characteristics of inbred 5720.

The data in Table 5 shows the relative hybrid performance of 5720 compared to two other Mo17 type inbred lines currently marketed by a Foundation Seed Stock Company. The comparisons of 5720 with the other inbred lines was conducted with 3 testers as indicated in Table 5. On the average, the 5720 hybrids yielded better than the other parents, with an overall advantage of 0.1 tons/hectare. The yield advantage was most pronounced when the test was grown in the southeastern quadrant of the corn belt, where corn diseases are typically present in high amounts. This advantage is reflective of the high degree of resistance this inbred contributes to its hybrids (Table 4). Hybrids involving 5720 have harvest moistures very similar to other hybrids involving Mo17. The excellent health of 5720 hybrids is reflected in the favorable scores for stay green, stalk lodging, root lodging, and field score. 5720 showed very distinct advantages in all of these categories (lower ratings are better than high ratings).

An RFLP profile of inbred 5720 is listed in Table 6. As far as is known, this pattern is unique from those of all other inbreds available.

Inbred seeds of 5720 have been placed on deposit pursuant to the terms of the Budapest Treaty at the American Type Culture Collection (ATCC), Rockville, Md., 20852, under deposit accession number 75339 on 2 November, 1992. A Plant Variety Protection Certificate has also been applied for with the United States Department of Agriculture.

Inbred 6022 was selected from a cross between two lines from the stiff stalk synthetic family available to Asgrow. Standard pedigree ear-row selection for acceptable agronomic types was performed throughout the generations of self pollination. Test crosses with unrelated inbred lines were made and evaluated over multiple locations. One subline within this population had good hybrid performance and appeared acceptable as a female parent. This subline was crossed with several non-related inbred lines and were evaluated throughout the central to northern US cornbelt. This inbred had good testcross performance with a number of unrelated inbred lines and excellent testcross performance with one specific tester.

The inbred 6022 produces hybrids which are well adapted to mid-north to northern regions of the US corn belt, producing hybrids with relative maturity of 100–105 days CCB. Inbred 6022 has good seed yield per se and excellent seed quality and thus serves as a good female parent.

The inbred 6022 has shown uniformity and stability for all traits as described in the following variety description information (Table 7). It has been self-pollinated and ear-rowed a sufficient number of generations with careful attention paid to uniformity of plant type to ensure genetic homozygosity and phenotypic stability. No variant traits are expected in 6022. Table 7 shows the morphological and other characteristics of inbred 6022.

The data in Table 8 shows the relative hybrid performance of 6022 compared to a number of stiff stalk inbred lines. These inbred lines are either Asgrow proprietary lines presently involved in commercial hybrids or those from a Foundation seed stock company from which Asgrow has a license. The comparisons of 6022 with the other stiff stalk inbred lines was conducted on 2 testers as indicated in Table 8. In all instances, the 6022 hybrids yielded more than the other stiff stalk parents, with an overall advantage of 0.4 T/ha. This yield advantage was maintained even though the 6022 hybrids were on the average, 1.6% drier, giving a Y:MO ratio advantage of 7.4. The stay green ratings were a bit less favorable (higher rating) that the other stiff stalks. For stalk lodging, root lodging, and field score, 6022 produced hybrids which were comparable to the other stiff stalk hybrids. 6022 also produced hybrids that are taller with high ear placement.

An RFLP profile of inbred 6022 is listed in Table 9. As far is known, this pattern is unique from those of all other inbreds available.

Inbred seeds of 6022 have been placed on deposit pursuant to the terms of the Budapest Treaty at the American Type Culture Collection (ATCC), Rockville, Md., 20852, under deposit accession number 75336 on 2 November, 1992. A Plant Variety Protection Certificate has also been applied for with the United States Department of Agriculture.

Inbred 7054 was selected from a cross between two lines from the stiff stalk synthetic family available to Asgrow. Standard pedigree ear-row selection for acceptable agronomic types was performed throughout the generations of self pollination. Test crosses with unrelated inbred lines were made and evaluated over multiple locations. One subline within this population had good hybrid performance and appeared acceptable as a female parent. This subline was crossed with several non-related inbred lines and were evaluated throughout the central US cornbelt. This inbred had very good testcross performance with a number of elated inbred lines.

The inbred 7054 produces hybrids which are well adapted to central and north central regions of the US corn belt, producing hybrids with relative maturity of 100–110 days CCB. Inbred 7054 has good seed yield per se and excellent seed quality and thus serves as a good female parent.

The inbred 7054 has shown uniformity and stability for all traits as described in the following variety description information (Table 10). It has been self-pollinated and ear-rowed a sufficient number of generations with careful attention paid to uniformity of plant type to ensure genetic homozygosity and phenotypic stability. No variant traits are expected in 7054. Table 10 shows the morphological and other characteristics of inbred 7054.

The data in Table 11 shows the relative hybrid performance of 7054 compared to a popular stiff stalk inbred line from a Foundation Seed Stock Company. This stiff stalk inbred line is from the same family as 7054, being derived from B73, a popular inbred line developed at Iowa State University. The comparisons of 7054 with the Foundation inbred was conducted on 2 testers as indicated in Table 11. In both instances, the 7054 hybrids yielded more than the other B73 parent, with an overall advantage of 0.3 T./ha. In addition, the 7054 hybrids were on the average, 0.2% drier which gives a Y:MO ratio advantage of 2.5. This Y:MO advantage was apparent in a number of other comparisons involving other B73 inbreds and several different tester inbreds. In most of the other traits, 7054 produced hybrids which were comparable to the other B73 hybrids.

An RFLP profile of inbred 7054 is listed in Table 12. As far as is known, this pattern is unique from those of all other inbreds available.

Inbred seeds of 7054 have been placed on deposit pursuant to the terms of the Budapest Treaty at the American Type Culture Collection (ATCC), Rockville, Md., 20852, under deposit accession number 75338 on 2 November, 1992. A Plant Variety Protection Certificate has also been applied for with the United States Department of Agriculture.

This invention is also directed to methods for producing a corn plant by crossing a first parent corn plant with a second parent corn plant wherein the first or second parent corn plant is an inbred corn plant selected from the group consisting of the lines 3087, 5720, 6022 and 7054. Further, both first and second parent corn plants may be from each respective inbred line. Thus any methods using the inbred corn lines of the present invention are part of the invention: self pollination, backcrosses, hybrid breeding and crosses to populations. Any plants produced using inbred corn lines 3087, 5720, 6022 or 7054 or a combination thereof as a parent are within the scope of this invention. Advantageously, the inbred corn lines are used in crosses with other corn varieties to produce first generation (F1) corn hybrid seed.

As used herein, the term "plant" includes plant cells, plant protoplasts, plant cell or tissue culture from which corn plants can be regenerated, plant calli, plant clumps, and plant cells that are intact in plants or parts of plants, such as pollen, flower, kernels, ears, cobs, leaves, husks, stalks, and the like.

Tissue culture of corn is described in European Patent Application, publication number 160,390. Corn tissue culture procedures are also described in Green and Rhodes, "Plant Regeneration in Tissue Culture of Maize," *Maize for Biological Research* (Plant Molecular Biology Association, Charlottesville, Va. 1982), at 367–372. Thus, another aspect of this invention is to provide for cells which upon growth and differentiation produce the inbred 3087, 5720, 6022 and 7054.

Although the foregoing invention has been described in some detail by way of illustration and example for purposes of clarity and understanding, one skilled in the art will appreciate that certain changes and modifications may be practiced within the scope of the invention, without departing from the true scope of the invention. In the foregoing specification the entire contents of all cited references are incorporated by reference.

TABLE 1

Morphological and other characteristics of Inbred 3087:
A. MATURITY
    Relative Maturity: Predicted maturities of hybrids 100–110 day CCB
    Heat units to silk: 1460 GDU
B. PLANT CHARACTERISTICS
    Plant height (to tassel tip): 203 cm
    Length of top ear internode: 11 cm
    Number of ears/stalk: 1
    Ear height (to base of top ear): 70 cm
    Number of tillers: Absent
    Cytoplasmic type: Normal
C. LEAF
    Color: Dark green
    Angle from stalk: 45 degrees
    Marginal waves: few
    Number of leaves (mature plant): 12
    Sheath pubescence: light
    Longitudinal creases: absent
    Length (ear node leaf): 62 cm
    Width 6.0 cm
D. TASSEL
    Number of lateral branches: 4–5
    Branch angle from central spike: >45 degrees
    Pollen shed (High, medium, low): light
    Peduncle length (top leaf to basal branch): 14 cm
    Anther color: pale green
    Glume color: green
E. EAR (husked ear unless otherwise stated)
    Length: 20 cm
    Weight: 95 g
    Midpoint diameter: 40 mm
    Silk color: pale green
    Husk extension (at harvest stage): medium (barely covering ear)
    Husk leaf length: short<8 cm
    Taper of ear (ear shape):straight, cylindrical
    Kernel row number: 10–12
    Husk color (fresh): light green
    Husk color (dry): buff
    Shank length: 9 cm
    Shank no. of internodes: 4
F. KERNEL (size from midpoint of dried ear).
    Length: 10 mm
    Width: 7 mm
    Thick: 5 mm
    Shape grade (%rounds): 60–80%
    Pericarp color: colorless
    Aleurone color: colorless
    Endosperm color: yellow
    Endosperm type: dent-medium hard texture
    Gm Wt/100 seeds (unsized): 30 g
G. COB
    Diameter at midpoint: 2.5 cm
    Strength: strong
    Color: white

TABLE 2

| | DATA OF HYBRIDS OF INBRED 3087 | | | | | | | | | |
|---|---|---|---|---|---|---|---|---|---|---|
| | YLD | MOIS | Y:MO | STL | RTL | SGR | FSC | HLWT | EHT | PHT |
| Tester 1/ 3087 | 10.29 | 17.83 | 59.33 | 3.00 | 1.22 | 5.40 | 4.77 | 73.80 | 97.48 | 251.5 |
| Tester 1/ ASGL3 | 9.81 | 18.80 | 53.62 | 3.40 | .85 | 4.48 | 4.74 | 73.75 | 99.58 | 246.5 |

TABLE 2-continued

DATA OF HYBRIDS OF INBRED 3087

| | YLD | MOIS | Y:MO | STL | RTL | SGR | FSC | HLWT | EHT | PHT |
|---|---|---|---|---|---|---|---|---|---|---|
| STD ERROR OF DIFF. | .161 | .177 | 1.003 | .521 | .198 | .372 | .173 | .383 | 1.396 | 1.375 |
| PROBABILITY NO DIFF. | .01 | .00 | .00 | .44 | .08 | .04 | .84 | .88 | .15 | .00 |
| NUMBER OF REPLICATIONS | 93 | 93 | 93 | 84 | 54 | 27 | 78 | 72 | 60 | 60 |
| Tester 1/ 3087 | 10.29 | 17.83 | 59.33 | 3.00 | 1.22 | 5.40 | 4.77 | 73.80 | 97.48 | 251.5 |
| Tester 1/ FSSL4 | 9.68 | 18.11 | 54.42 | 2.55 | .91 | 6.18 | 5.22 | 73.62 | 83.52 | 218.9 |
| STD ERROR OF DIFF. | .185 | .166 | 1.259 | .378 | .154 | .389 | .118 | .399 | 2.022 | 3.267 |
| PROBABILITY NO DIFF. | .00 | .11 | .00 | .24 | .06 | .08 | .00 | .65 | .00 | .00 |
| NUMBER OF REPLICATIONS | 93 | 93 | 93 | 84 | 54 | 27 | 78 | 72 | 60 | 60 |
| Tester 2/ 3087 | 9.21 | 18.24 | 51.60 | 3.63 | 1.31 | 5.08 | 5.61 | 75.61 | 97.31 | 258.9 |
| Tester 2/ FSSL4 | 9.17 | 17.36 | 53.41 | 3.48 | 1.19 | 6.00 | 5.84 | 74.76 | 84.44 | 221.7 |
| STD ERROR OF DIFF. | .219 | .351 | 1.422 | .578 | .151 | .300 | .191 | .407 | 1.849 | 3.244 |
| PROBABILITY NO DIFF. | .86 | .02 | .22 | .80 | .46 | .03 | .25 | .05 | .00 | .00 |
| NUMBER OF REPLICATIONS | 46 | 46 | 46 | 42 | 26 | 12 | 44 | 38 | 36 | 36 |

TABLE 3

Inbred 3087 RFLP Characterization

| Probe/enzyme | Fragment MW(s) in kilo base pairs |
|---|---|
| BNL 5.62/H | 14.863 |
|  | 9.145 |
| UMC11/H | 8.750 |
|  | 7.107 |
|  | 1.429 |
| UMC6/H | 7.205 |
|  | 2.585 |
| UMC121/E1 | 3.564 |
| UMC15/E5 | 10.161 |
| BNL 5.71/H | 5.944 |
| UMC62/E5 | 3.813 |
| BNL7.61/E5 | 4.739 |
| UMC48/E1 | 7.413 |
| BNL5.09/E5 | 17.202 |
| UMC44/E1 | 6.934 |
|  | 2.284 |
| UMC19/E5 | 9.487 |
| UMC114/E5 | 11.000 |
| BNL5.37/E1 | 13.093 |
|  | 2.068 |
| UMC130/E5 | 8.352 |
| UMC155/E5 | 9.373 |
| UMC68/E5 | 10.632 |
| UMC149/S | 7.419 |
| BNL6.32/H | 10.632 |
| BNL12.06/H | 6.439 |

Enzymes: H = Hind III, E1 = EcoR1, E5 = EcoR5

TABLE 4

Morphological and other characteristics of inbred 5720:
A. MATURITY
  Relative Maturity: Predicted maturities of hybrids 107–116 day CCB
  Heat units to shedding: 1554 GDU
  Heat units to silk: 1596 GDU
  Amount of replication supporting above data: 16 reps over 2 years.
B. PLANT CHARACTERISTICS
  Plant height (to tassel tip): 220 cm
  Length of top ear internode: 17 cm
  Number of ears/stalk: 1
  Ear height (to base of top ear): 83 cm
  Number of tillers: Absent
  Cytoplasmic type: Normal
C. LEAF
  Color: Light green
  Angle from stalk: 20–45 degrees
  Marginal waves: Few marginal waves and moderate in degree
  Number of leaves (mature plant): 12
  Sheath pubescence: light
  Longitudinal creases: Few and not pronounced
  Length (ear node leaf): 80 cm
  Width: 9 cm
D. TASSEL
  Number of lateral branches: 6–10
  Branch angle from central spike: 30 degrees
  Pollen shed (High, medium, low): medium
  Peduncle length (top leaf to basal branch): 3–5 cm
  Anther color: light green
  Glume color: light green
E. EAR (husked ear unless otherwise stated)
  Length: 14 cm
  Weight: 68 gm
  Midpoint diameter: 35 cm
  Silk color: light green
  Husk extension (at harvest stage): long 8–10 cm
  Husk leaf length: short<8cm
  Taper of ear (ear shape):slightly tapered Kernel row number: 12
Husk color (fresh): light green
Husk color (dry): buff
Shank length: 18 cm
Shank no. of internodes: 7
F. KERNEL (size from midpoint of dried ear).
Length: 12 mm
Width: 8 mm
Thick: 5 mm
Shape grade:
  10.0% small rounds
  37.7% medium rounds
  9.8% large rounds
  1.4% small flats
  16.8% medium flats
  24.2% large flats
Pericarp color: colorless
Aleurone color: colorless
Endosperm color: yellow
Endosperm type: dent-medium soft texture
Gm Wt/100 seeds (unsized): 27 g
G. COB
  Diameter at midpoint: 23 mm
  Strength: weak
  Color: red
H. DISEASES
  Resistant to northern corn leaf blight race 1, *Setosphaeria turcica* (Luttrell) Leonard and Suggs. Homozygous for Ht1 gene.
  Resistant to northern corn leaf blight race 2, *Setosphaeria turcica* (Luttrell) Leonard and Suggs. Rated 2.5 on 1 (res.) to 9 (susc.) scale, in 2 reps data over two years.
  Resistant to southern corn leaf blight race 0, *Cochliobolus heterostrophus* (Srechs.) Drechs. Rated 3.5 on a 1 to 9 scale, for 2 reps of data over two years.
  Resistant to gray leaf spot, *Cercospora zeae-maydis* Tehon and Daniels. Rated 2.9 on a 2 to 9 scale, for 4 reps of data over two years.
  Resistant to Stewart's bacterial blight, *Erwinia sterartii* (Smith) Dye. Rated 1.4 on a 1 to 9 scale, for 3 reps of data over two years.
  Resistant to Goss's bacterial blight, *Clavibacter michiganense* subsp. *nebraskense* (Schuster el. at.) Davis et. al. Rated 1.0 on a 1 to 9 scale, for 1 rep of data in one year.
I. INSECTS
  Hybrids involving 5720 have shown excellent tolerance to second brood of European corn borer, as measured by visual integrity of the stalk at harvest.

TABLE 5

| | YLD | MOIS | Y:MO | STL | RTL | SGR | FSC | HLWT | EHT | PHT |
|---|---|---|---|---|---|---|---|---|---|---|
| DATA OF HYBRIDS OF INBRED 5720 | | | | | | | | | | |
| Tester 1/ 5720 | 9.76 | 17.40 | 57.44 | 3.03 | 1.08 | 3.92 | 4.14 | 76.74 | 91.78 | 258.1 |
| Tester 1/ FSSL3 | 9.53 | 17.29 | 56.21 | 4.88 | 1.73 | 5.83 | 5.89 | 74.84 | 104.9 | 254.1 |
| STD ERROR OF DIFF. | .182 | .207 | 1.138 | .963 | .523 | .154 | .241 | .503 | 2.030 | 2.134 |
| PROBABILITY NO DIFF. | .22 | .63 | .29 | .07 | .24 | .00 | .00 | .00 | .00 | .08 |
| NUMBER OF REPLICATIONS | 46 | 46 | 46 | 42 | 26 | 12 | 44 | 38 | 36 | 36 |
| Tester 2/ 5720 | 9.86 | 18.63 | 54.93 | 3.47 | .86 | 2.80 | 3.51 | 76.32 | 96.89 | 263.6 |
| Tester 2/ FSSL3 | 9.99 | 19.31 | 53.91 | 3.58 | 1.05 | 4.00 | 4.32 | 75.78 | 106.6 | 268.7 |
| STD ERROR OF DIFF. | .195 | .169 | 1.025 | .425 | .090 | .279 | .234 | .307 | 2.270 | 2.907 |
| PROBABILITY NO DIFF. | .52 | .00 | .33 | .79 | .06 | .00 | .00 | .09 | .00 | .10 |
| NUMBER OF REPLICATIONS | 72 | 72 | 72 | 56 | 28 | 40 | 48 | 54 | 28 | 28 |
| Tester 3/ 5720 | 9.12 | 17.65 | 52.97 | 2.99 | 1.00 | 3.17 | 4.14 | 75.96 | 101.4 | 263.8 |
| Tester 3/ ASGL4 | 9.11 | 17.92 | 51.88 | 6.02 | 1.92 | 4.75 | 5.64 | 76.86 | 105.3 | 265.3 |
| STD ERROR OF DIFF. | .184 | .231 | 1.192 | 1.029 | .396 | .417 | .174 | .457 | 1.962 | 2.166 |
| PROBABILITY NO DIFF. | .97 | .27 | .37 | .01 | .04 | .01 | .00 | .06 | .06 | .52 |
| NUMBER OF REPLICATIONS | 46 | 46 | 46 | 42 | 26 | 12 | 44 | 38 | 36 | 36 |

TABLE 6

| Probe/enzyme | Fragment MW(s) in kilo base pairs |
|---|---|
| BNL 5.62/H | 14.863 |
| | 9.145 |
| UMC11/H | 8.750 |
| | 4.842 |
| UMC6/H | 4.293 |
| | 2.585 |
| UMC121/E1 | 6.951 |
| | 4.954 |

Inbred 5720 RFLP Characterization

TABLE 6-continued

Inbred 5720 RFLP Characterization

| Probe/enzyme | Fragment MW(s) in kilo base pairs |
|---|---|
| UMC15/E5 | 6.475 |
| BNL 5.71/H | 14.232 |
| UMC62/E5 | 8.950 |
| BNL7.61/E5 | 4.739 |
| UMC48/E1 | 10.461 |
| BNL5.09/E5 | 9.717 |
| UMC44/E1 | 12.853 |
|  | 2.284 |
| UMC19/E5 | 9.487 |
| UMC114/E5 | 22.000 |
| BNL5.37/E1 | 9.100 |
|  | 2.276 |
| UMC130/E5 | 12.556 |
| UMC155/E5 | 6.132 |
| UMC68/E5 | 5.447 |
| UMC149/S | 3.809 |
| BNL6.32/H | 7.304 |
| BNL12.06/H | 18.757 |

Enzymes: H = Hind III, E1 = EcoR1, E5 = EcoR5

TABLE 7

Morphological and other characteristics of inbred 6022:
A. MATURITY
  Relative Maturity: Predicted maturities of hybrids 100–110 day CCB
  Heat units to shedding: 1450 GDU
  Heat units to silk: 1478 GDU
B. PLANT CHARACTERISTICS
  Plant height (to tassel tip): 198 cm
  Length of top ear internode: 75 cm
  Number of ears/stalk: Slight 2 eared tendency
  Ear height (to base of top ear): 70 cm
  Number of tillers: Absent
  Cytoplasmic type: Normal
C. LEAF
  Color: Green
  Angle from stalk: 45 degrees
  Marginal waves: few
  Number of leaves (mature plant): 16
  Sheath pubescence: medium
  Longitudinal creases: few
  Length (ear node leaf): 74 cm
  Width: 79 mm
D. TASSEL
  Number of lateral branches: 5
  Branch angle from central spike: Semi-erect
  Pollen shed (High, medium, low): medium
  Peduncle length (top leaf to basal branch): 5 cm
  Anther color: light purple
  Glume color: green
E. EAR (husked ear unless otherwise stated)
  Length: 16.3 cm
  Weight: 110 g
  Midpoint diameter: 3.75 cm
  Silk color: light green
  Husk extension (at harvest stage): medium (barely covering the ear)
  Husk leaf length: medium 8–15 cm
  Taper of ear (ear shape):straight, cylindrical
  Kernel row number: 12–14
  Husk color (fresh): light green
  Husk color (dry): buff
F. KERNEL (size from midpoint of dried ear).
  Length: 10 mm
  Width: 9 mm
  Thick: 5 mm
  Shape grade (% rounds): 20–40%
  Pericarp color: clear
  Aleurone color: white
  Endosperm color: yellow
  Endosperm type: dent/normal
  Gm Wt/100 seeds (unsized): 25 g
G. COB
  Diameter at midpoint: 2.5 cm
  Strength: strong
  Color: red

TABLE 8

DATA OF HYBRIDS OF INBRED 6022

|  | YLD | MOIS | Y:MO | STL | RTL | SGR | FSC | HLWT | EHT | PHT |
|---|---|---|---|---|---|---|---|---|---|---|
| Tester 1/ TESTER 1 | 9.68 | 16.14 | 61.17 | 3.01 | .96 | 6.48 | 5.63 | 74.12 | 91.20 | 223.4 |
| FSSL2/ TESTER | 9.55 | 18.56 | 52.20 | 2.75 | .83 | 5.78 | 5.07 | 74.62 | 80.80 | 220.4 |
| STD ERROR OF DIFF. | .127 | .153 | 1.011 | .406 | .081 | .399 | .157 | .486 | 1.685 | 1.748 |
| PROBABILITY NO DIFF. | .31 | .00 | .00 | .53 | .13 | .12 | .00 | .31 | .00 | .10 |
| NUMBER OF REPLICATIONS | 93 | 93 | 93 | 84 | 54 | 27 | 78 | 72 | 60 | 60 |
| 6022/ TESTER 1 | 9.68 | 16.14 | 61.17 | 3.01 | .96 | 6.48 | 5.63 | 74.12 | 91.20 | 223.4 |
| ASGL1/ TESTER 1 | 8.99 | 17.46 | 52.18 | 3.42 | .97 | 6.59 | 5.48 | 74.62 | 80.10 | 208.9 |
| STD ERROR OF DIFF. | .142 | .133 | 1.024 | .316 | .062 | .310 | .139 | .329 | 1.420 | 2.755 |
| PROBABILITY NO DIFF. | .00 | .00 | .00 | .21 | .91 | .73 | .29 | .14 | .00 | .00 |

TABLE 8-continued

| DATA OF HYBRIDS OF INBRED 6022 | | | | | | | | | | |
|---|---|---|---|---|---|---|---|---|---|---|
| | YLD | MOIS | Y:MO | STL | RTL | SGR | FSC | HLWT | EHT | PHT |
| NUMBER OF REPLICATIONS | 93 | 93 | 93 | 84 | 54 | 27 | 78 | 72 | 60 | 60 |
| 6022/ TESTER 2 | 9.39 | 16.98 | 56.47 | 3.72 | 2.50 | 6.00 | 5.75 | 74.75 | 118.9 | 278.2 |
| ASGL2/ TESTER 2 | 9.11 | 17.92 | 51.88 | 6.02 | 1.92 | 4.75 | 5.64 | 76.86 | 105.3 | 265.3 |
| STD ERROR OF DIFF. | .160 | .185 | 1.284 | .936 | .434 | .382 | .186 | .361 | 1.703 | 2.003 |
| PROBABILITY NO DIFF. | .09 | .00 | .00 | .02 | .21 | .02 | .55 | .00 | .00 | .00 |
| NUMBER OF REPLICATIONS | 46 | 46 | 46 | 42 | 26 | 12 | 44 | 38 | 36 | 36 |

TABLE 9

Inbred 6022 RFLP Characterization

| Probe/enzyme | Fragment MW(s) in kilo base pairs |
|---|---|
| BNL 5.62/H | 14.863 |
| | 9.145 |
| UMC11/H | 8.750 |
| UMC6/H | 4.293 |
| | 2.585 |
| UMC121/E1 | 2.052 |
| UMC15/E5 | 6.475 |
| BNL 5.71/H | 14.232 |
| UMC62/E5 | 3.813 |
| BNL7.61/E5 | 10.737 |
| UMC48/E1 | 10.461 |
| BNL5.09/E5 | 9.717 |
| UMC44/E1 | 12.853 |
| | 2.284 |
| UMC19/E5 | 9.487 |
| UMC114/E5 | 22.000 |
| BNL5.37/E1 | 5.200 |
| | 2.068 |
| UMC130/E5 | 5.447 |
| UMC155/E5 | 6.132 |
| UMC68/E5 | 5.447 |
| UMC149/S | 3.809 |
| BNL6.32/H | 10.632 |
| BNL12.06/H | 4.401 |

Enzymes: H = Hind III, E1 = EcoR1, E5 = EcoR5

TABLE 10

Morphological and other characteristics inbred 7054:
A. MATURITY
  Relative Maturity: Predicted maturities of hybrids 100–110 day CCB
  Heat units to shedding: 1450 GDU
  Heat units to silk: 1465 GDU
  Amount of replication supporting above data: 2 years, 8 sites (16 reps).
B. PLANT CHARACTERISTICS
  Plant height (to tassel tip): 200 cm
  Length of top ear internode: 12 cm
  Number of ears/stalk: 1
  Ear height (to base of top ear): 80 cm
  Number of tillers: Few
  Cytoplasmic type: Normal
C. LEAF
  Color: Dark green
  Angle from stalk: 30 degrees
  Marginal waves: None
  Number of leaves (mature plant): 12
  Sheath pubescence: light
  Longitudinal creases: absent
  Length (ear node leaf): 72 cm
  Width: 83 mm
D. TASSEL
  Number of lateral branches: 5–6
  Branch angle from central spike: 30–40 degrees
  Pollen shed (High, medium, low): medium
  Peduncle length (top leaf to basal branch): 12 cm
  Anther color: pink
  Glume color: purple and green
E. EAR (husked ear unless otherwise stated)
  Length: 15 cm
  Weight: 85 g
  Midpoint diameter: 4.25 cm
  Silk color: light green
  Husk extension (at harvest stage): short (barely covering ear)
  Husk leaf length: short (<8 cm)
  Taper of ear (ear shape):straight, cylindrical
  Kernel row number: 14–16
  Husk color (fresh): medium green
  Husk color (dry): buff
  Shank length: 7 cm
  Shank no. of internodes: 6
F. KERNEL (size from midpoint of dried ear).
  Length: 10 mm
  Width: 8 mm
  Thick: 4 mm
  Shape grade (% rounds): 20–40%
  Pericarp color: clear
  Aleurone color: white
  Endosperm color: yellow
  Endosperm type: dent/normal
  Gm Wt/100 seeds (unsized): 25 g
G. COB
  Diameter at midpoint: 2.6 cm
  Strength: strong
  Color: red

H. DISEASES

Southern corn leaf blight: Moderately resistant for a stiff stalk line
overall rating: susceptible.
Northern corn leaf blight: Moderately susceptible
Gray leaf spot: Susceptible
Stewart's wilt: Moderately resistant for a stiff stalk line
overall rating: susceptible.

TABLE 11

DATA OF HYBRIDS OF INBRED 7054

|  | YLD | MOIS | Y:MO | STL | RTL | SGR | FSC | HLWT | EHT | PHT |
|---|---|---|---|---|---|---|---|---|---|---|
| 7054/TESTER 1 | 10.64 | 18.83 | 59.26 | 1.94 | .86 | 6.00 | 4.70 | 73.20 | 97.18 | 250.6 |
| FSSL1/TESTER 1 | 10.27 | 19.46 | 55.37 | 2.70 | 1.00 | 4.75 | 4.73 | 72.78 | 96.93 | 256.2 |
| STD ERROR OF DIFF. | .129 | .154 | .563 | .497 | .092 | .250 | .215 | .358 | 1.348 | 2.131 |
| PROBABILITY NO DIFF. | .01 | .00 | .00 | .14 | .17 | .13 | .88 | .20 | .86 | .02 |
| NUMBER OF REPLICATIONS | 40 | 40 | 40 | 36 | 14 | 4 | 30 | 34 | 28 | 28 |
| 7054/TESTER 2 | 9.57 | 19.62 | 50.14 | 2.38 | 1.09 | 3.23 | 3.75 | 74.30 | 98.79 | 254.5 |
| FSSL1/TESTER 2 | 9.19 | 19.40 | 48.84 | 2.06 | .87 | 3.29 | 3.72 | 75.83 | 94.02 | 258.2 |
| STD ERROR OF DIFF. | .125 | .164 | .789 | .348 | .108 | .203 | .171 | .473 | 1.189 | 1.566 |
| PROBABILITY NO DIFF. | .01 | .18 | .11 | .38 | .06 | .75 | .88 | .00 | .00 | .03 |
| NUMBER OF REPLICATIONS | 93 | 93 | 93 | 84 | 54 | 27 | 78 | 72 | 60 | 60 |

TABLE 12

Inbred 7054 RFLP Characterization

| Probe/enzyme | Fragment MW(s) in kilo base pairs |
|---|---|
| BNL 5.62/H | 14.863 |
| UMC11/H | 8.750 |
| UMC6/H | 7.205 |
|  | 5.610 |
|  | 4.293 |
|  | 2.585 |
| UMC121/E1 | 9.891 |
|  | 6.951 |
|  | 4.954 |
| UMC15/E5 | 6.475 |
| BNL 5.71/H | 14.232 |
|  | 3.417 |
| UMC62/E5 | 3.813 |
| BNL7.61/E5 | 4.739 |
| UMC48/E1 | 10.461 |
| BNL5.09/E5 | 2.965 |
| UMC44/E1 | 12.853 |
|  | 2.284 |
| UMC19/E5 | 6.439 |
| UMC114/E5 | 11.000 |
| BNL5.37/E1 | 8.260 |
|  | 2.068 |
| UMC130/E5 | 12.556 |
| UMC155/E5 | 7.118 |
| UMC68/E5 | 13.302 |
| UMC149/S | 3.809 |
| BNL6.32/H | 8.688 |
| BNL12.06/H | 4.401 |

Enzymes: H = Hind III, E1 = EcoR1, E5 = EcoR5

I claim:

1. A corn seed or seeds designated 7054, a sample of said seeds having been deposited as ATCC accession No. 75338.

2. A corn plant or plants produced by growing the seed of claim 1.

3. Pollen of the plant or plants of claim 2.

4. An ovule or the plant or plants of claim 2.

5. A corn plant having all the physiological and morphological characteristics of the corn plant or plants of claim 2.

6. Tissue culture of regenerable cells of the plant or plants of claim 2.

7. A corn plant regenerated from the regenerable cells of a tissue culture of claim 6, said plant possessing all the physiological and morphological characteristics of the corn plant designated 7054, a seeds sample of corn plant 7054 having been deposited as ATCC accession No. 75338.

8. A method to produce hybrid corn seed comprising the steps of:

a) planting in pollinating proximity seed of corn inbred line 7054, a seed sample of having been deposited as ATCC accession No. 75338, and a second corn inbred line;

b) cultivating corn plants resulting from said seed until said plants bear flowers;

c) emasculating or inactivating the male flower of the plants of either one or the other corn lines to produce female corn plants;

d) allowing cross pollination to occurr between said inbred lines, and;

e) harvesting seeds produced on said female plants.

9. A first generation ($F_1$) hybrid corn plant produced by growing said hybrid corn seed of claim 8.

10. A tissue culture initiated from the cells of the corn plant according to claim 9.

11. Seed produced by a hybrid corn plant of claim 9, said hybrid plant having as one of its parents inbred corn plant 7054, a seed sample of which having been deposited as ATCC accession No. 75338.

* * * * *